(12) United States Patent
Stranjak

(10) Patent No.: US 12,082,980 B2
(45) Date of Patent: Sep. 10, 2024

(54) IMAGING DEVICE AND METHOD OF OPERATING THE SAME

(71) Applicant: Siemens Healthcare GmbH, Erlangen (DE)

(72) Inventor: Armin Stranjak, Uttenreuth (DE)

(73) Assignee: Siemens Healthineers AG, Forchheim (DE)

(*) Notice: Subject to any disclaimer, the term of this patent is extended or adjusted under 35 U.S.C. 154(b) by 795 days.

(21) Appl. No.: 17/081,964

(22) Filed: Oct. 27, 2020

(65) Prior Publication Data

US 2021/0121262 A1 Apr. 29, 2021

(30) Foreign Application Priority Data

Oct. 28, 2019 (EP) .................................. 19205641

(51) Int. Cl.
*A61B 90/00* (2016.01)
*A61B 17/34* (2006.01)

(52) U.S. Cl.
CPC .......... *A61B 90/37* (2016.02); *A61B 17/3403* (2013.01); *A61B 2090/374* (2016.02); *A61B 2090/3762* (2016.02)

(58) Field of Classification Search
CPC ................ A61B 90/37; A61B 17/3403; A61B 2090/374; A61B 2090/3762
See application file for complete search history.

(56) References Cited

U.S. PATENT DOCUMENTS

2016/0166336 A1* 6/2016 Razzaque .............. A61B 34/20
606/130

OTHER PUBLICATIONS

Kim, C., Chang, D., Petrisor, D., Chirikjian, G., Han, M., & Stoianovici, D. (2013). Ultrasound probe and needle-guide calibration for robotic ultrasound scanning and needle targeting. IEEE Transactions on Biomedical Engineering, 60(6), 1728-1734. (Year: 2013).*
European Search Report for European Application No. 19205641. 4-1122 dated May 6, 2020.
Gibbons, Erin P., et al. "Overcoming pubic arch interference with free-hand needle placement in men undergoing prostate brachytherapy." Brachytherapy 8.1 (2009): 74-78.

* cited by examiner

*Primary Examiner* — Bijan Mapar
(74) *Attorney, Agent, or Firm* — Lempia Summerfield Katz LLC

(57) ABSTRACT

A method of operating an imaging device and a corresponding device are provided. The method is guidable by N elongate guide members and includes: establishing N+1 first spatial imaging planes each having an intersection with each of the N elongate guide members; determining a spatial orientation of each of the N elongate guide members based on the intersection of the respective guide member with each of the first spatial imaging planes; and identifying at least one second spatial imaging plane along or perpendicular to the respective determined spatial orientation of each of the N elongate guide members.

17 Claims, 3 Drawing Sheets

IMAGING DEVICE AND METHOD OF OPERATING THE SAME

This application claims the benefit of European Patent Application No. EP 19205641.4, filed on Oct. 28, 2019, which is hereby incorporated by reference in its entirety.

FIELD

Various embodiments of the invention relate to an imaging device and a method of operating the same. Various embodiments relate in particular to imaging in support of clinical intervention procedures.

BACKGROUND

Tissue removal, fluid removal, or ablation are ones of typical clinical interventions where a needle is inserted into a patient's body in order to access an internal body portion of interest. Tissue removal (e.g., biopsy) from a body is usually performed in order to examine the presence, cause, or extent of a disease in body portions such as, for example, in breast, liver, kidney, skin biopsy, etc. Fluid removal (e.g., paracentesis) from a body is usually performed in order to remove accumulated unwanted fluid from body portions such as abdomen or lungs. Ablation is usually performed in the course of cancer treatment, where a tumor is exposed to energy of electromagnetic or radio waves or ethanol injections to damage cancer cells.

In all of the above clinical interventions, the trajectory/path of the needle between an entry point (e.g., skin surface) and a targeted body part is usually determined before the intervention takes place. Once the path is defined, the needle is to follow this given path.

In known interventional procedures, the needle is inserted and controlled manually by an interventionist. As such, the needle is prone to certain deviation from the given path and is to be monitored constantly by the interventionist using visual monitoring of an image slice aligned with the predefined path. Continuous monitoring of the movement and path of the needle is thus a crucial part of the intervention.

For example, an intersection between the needle and the image slice may be shown to the interventionist. As soon as the needle deviates from the given path or even disappears from the image slice due to human error, the needle is to be adjusted manually and returned to the predefined path in order to avoid unintentional damage to the neighboring tissue or body parts on the path of the needle. This process provides that the needle stays on the predefined path all the time, but is error-prone, slow, and this leads to an unpleasant procedure for a patient and a tiring and long procedure for everybody.

However, if an arbitrary path is allowed when the path is not defined in advance and the needle would target a region (e.g., an accumulation of liquid, etc.) rather than a point target, this method becomes insufficient. In such a case, constant monitoring usually requires another person (e.g., such as a scanner software operator) to continuously adjust the spatial position of the image slice in order to follow the path of the needle during the intervention. This is done manually without a guarantee that the needle will be constantly followed, and for that reason, intensive coordination between interventionist and operator is to be provided in order to provide satisfactory needle visibility on the slice.

This technique is even more error-prone when guidance by multiple needles is to be provided, since some interventions involve more than one needle in the clinical intervention procedure at the same time. When multiple needles are to be monitored in parallel, this process is particularly slow.

SUMMARY AND DESCRIPTION

In view of the above, there is a continued need in the art for methods and devices that address some of the above needs.

According to a first aspect, a method for operating an imaging device is provided. The method is guidable by N elongate guide members and includes: a) establishing N+1 first spatial imaging planes each having an intersection with each of the N elongate guide members; b) determining a spatial orientation of each of the N elongate guide members based on the intersection of the respective guide member with each of the first spatial imaging planes; and c) identifying at least one second spatial imaging plane along or perpendicular to the respective determined spatial orientation of each of the N elongate guide members.

The method may further include, in response to a trigger event, d) detecting if each of the first spatial imaging planes still has an intersection with each of the N elongate guide members.

The trigger event may include at least one of a lapse of a timer and/or an indication that at least one of the intersections 410 has moved within the corresponding first spatial imaging plane in excess of a given threshold.

The method may further include: in response to detecting that each of the first spatial imaging planes has an intersection with each of the N elongate guide members, proceeding at act b).

The method may further include, in response to detecting that at least one of the first spatial imaging planes does not have an intersection with each of the N elongate guide members; displacing the at least one of the first spatial imaging planes not having an intersection with each of the N elongate guide members to be located closer to, in accordance with at least one of the determined spatial orientations, one of the first spatial imaging planes having an intersection with each of the N elongate guide members; and proceeding at act d).

The one of the first spatial imaging planes having an intersection with each of the N elongate guide members may have a largest spacing, in accordance with the at least one of the determined spatial orientations, relative to the at least one of the first spatial imaging planes not having an intersection with each of the N elongate guide members.

The method may further include displaying the at least one second spatial imaging plane of at least one of the N elongate guide members.

Identifying at least one second spatial imaging plane may include identifying three mutually orthogonal second spatial imaging planes along or perpendicular to the respective determined spatial orientation of each of the N elongate guide members.

The number N of elongate guide members may be a positive integer.

The number N of elongate guide members may equal 1.

The elongate guide members may include a surgical needle.

The first spatial imaging planes may be arranged parallel to one another.

According to a second aspect, an imaging device is provided. The imaging device is for performing a method being guidable by N elongate guide members and includes at least one processing device being arranged for: a) establishing N+1 first spatial imaging planes each having an intersection with each of the N elongate guide members; b) determining a spatial orientation of each of the N elongate guide members based on the intersection of the respective guide member with each of the first spatial imaging planes; and c) identifying at least one second spatial imaging plane along or perpendicular to the respective determined spatial orientation of each of the N elongate guide members.

The at least one processing device may further be arranged for performing the method of various embodiments.

BRIEF DESCRIPTION OF THE DRAWINGS

Embodiments will be described with reference to the accompanying drawings, in which the same or similar reference numerals designate the same or similar elements.

DETAILED DESCRIPTION

Figure 1:
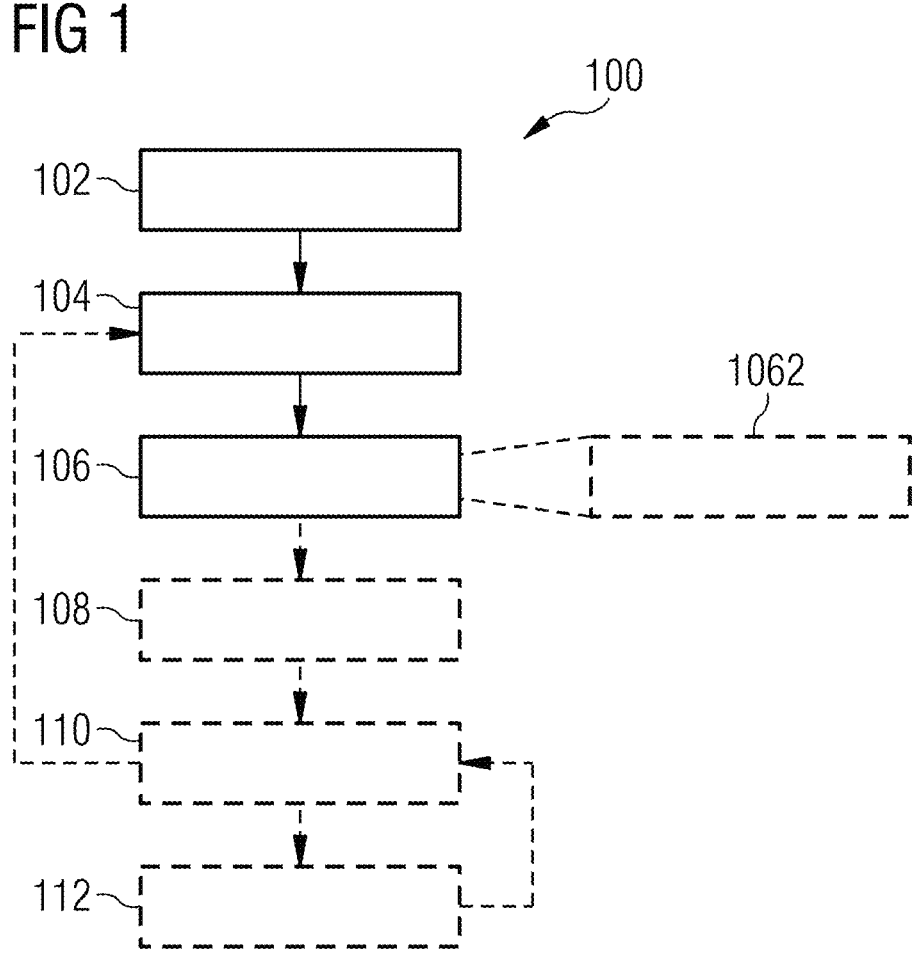
FIG. 1 illustrates a method according to various embodiments.

Exemplary embodiments will now be described with reference to the drawings. While some embodiments will be described in the context of specific fields of application, the embodiments are not limited to this field of application. Further, the features of the various embodiments may be combined with each other unless specifically stated otherwise.

The drawings are to be regarded as being schematic representations, and elements illustrated in the drawings are not necessarily shown to scale. Rather, the various elements are represented such that their function and general purpose become apparent to a person skilled in the art.

FIG. 1 illustrates a method 100 according to various embodiments.

The method 100 is guidable by N elongate guide members 300 and seeks to provide meaningful real-time visualization of the elongate guide members 300 within a surrounding body portion of interest during a clinical intervention.

The method 100 provisions interventionists with real-time digital images by systematic positioning of two-dimensional planes (e.g., image slices) in a three-dimensional image space, such as supplied by various spatial imaging techniques like computer tomography (CT) or magnetic resonance imaging (MRI), and providing the real-time digital images corresponding to these image slices. The systematic positioning of the image slices is guided by the elongate guide members 300.

As used herein, "guidable" may relate to a capability of being guided.

As used herein, "elongate" may relate to "long", "linear" or "having a much greater length than width, diameter or cross-section".

As used herein, a "guide member" may, for example, relate to a long and thin member such as a surgical needle that may be used to guide a clinical intervention procedure into or to a point target or target region.

For example, the elongate guide members 300 may include a surgical needle.

For example, the number N of elongate guide members 300 may be a positive integer, and may, for example, equal 1.

As indicated by solid lines in FIG. 1, a most general embodiment of the method 100 includes method acts 102, 104, and 106.

Act 102 involves a) establishing N+1 first spatial imaging planes 400 (e.g., tracking slices) each having an intersection 410 with each of the N elongate guide members 300.

As used herein, a "first spatial imaging plane" may relate to an image slice, as previously mentioned, that is used for tracking the N elongate guide members 300 during a clinical intervention procedure.

For example, the first spatial imaging planes 400 may be arranged parallel to one another.

As used herein, "parallel" may relate to a spatial arrangement of two-dimensional planes in a three-dimensional space, where the planes do not touch each other.

As used herein, an "intersection" may relate to point of penetration of a plane (e.g., tracking slice 400) by a line (e.g., needle 300).

Those skilled in the art will appreciate that performing a) may involve applying known image processing algorithms to non-parallel or parallel tracking slices 400 such as those provided by the above-mentioned spatial imaging techniques, for example.

Act 104 involves b) determining a spatial orientation of each of the N elongate guide members 300 based on the intersection 410 of the respective guide member with each of the first spatial imaging planes 400.

Act 106 involves c) identifying at least one second spatial imaging plane 500 (e.g., display slice) along or perpendicular to the respective determined spatial orientation of each of the N elongate guide members 300.

As used herein, a "second spatial imaging plane" may relate to an image slice, as previously mentioned, that is used for displaying the N elongate guide members 300 within a context of a surrounding body portion of interest during a clinical intervention procedure.

This provides a continuous optimal positioning of the at least one display slice 500 associated with the respective needle 300 in both single and multiple needle scenarios, which are explained next.

Single Needle Scenario

Figure 2:
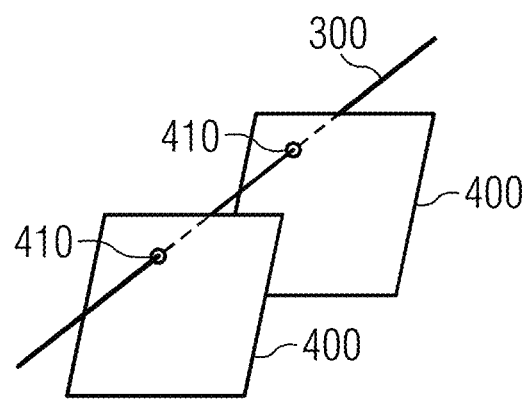
FIG. 2 illustrates circumstances of the method according to various embodiments concerning the establishing and determining acts of the method of FIG. 1 and involving N=1 elongate guide members and N+1=2 first spatial imaging planes.

FIG. 2 illustrates circumstances of the method 100 according to various embodiments concerning the establishing 102 and determining 104 acts. The case illustrated in FIG. 2 involves N=1 elongate guide members 300 (e.g., needles) and N+1=2 first spatial imaging planes 400 (e.g., tracking slices).

According to FIG. 2, the two tracking slices 400 are established to respectively have an intersection 410 with the single needle 300.

In general, the tracking slices 400 may have arbitrary spatial orientations, and may, for example, be in parallel to one another.

For example, the tracking slices 400 may have an arbitrary distance with respect to each other, as long as the respective tracking slice 400 intersects with the needle 300.

This, for example, reduces a computational complexity of the method 100 and simplifies subsequent calculations in connection with act 104 (see below), as various spatial imaging techniques readily provide parallel image slices, which may be used as tracking slices 400.

Those skilled in the art will appreciate that it is possible to determine a spatial orientation of the needle 300 using simple geometry, as indicated by the line drawn through the two known intersections 410 with the tracking slices 400. The intersections 410 may be represented by three-dimensional coordinates.

More specifically, in a three-dimensional Cartesian space, a linear function or line (x, y, z) passing through points $(x_0, y_0, z_0)$ and $(x_1, y_1, z_1)$ may be defined as follows:

$$x = x_0 + (x_1 - x_0)t$$

$$y = y_0 + (y_1 - y_0)t$$

$$z = z_0 + (z_1 - z_0)t$$

$$\forall -\infty < t < +\infty$$

A spatial orientation of the line is thus given by the vector:

$$(x_1 - x_0, y_1 - y_0, z_1 - z_0)$$

Multiple Needle Scenario

Regarding scenarios involving multiple needles 300, the main challenge is to unambiguously identify a respective needle 300 based on intersections 410 of the respective needle 300 with each of the tracking slices 400.

Figure 3:
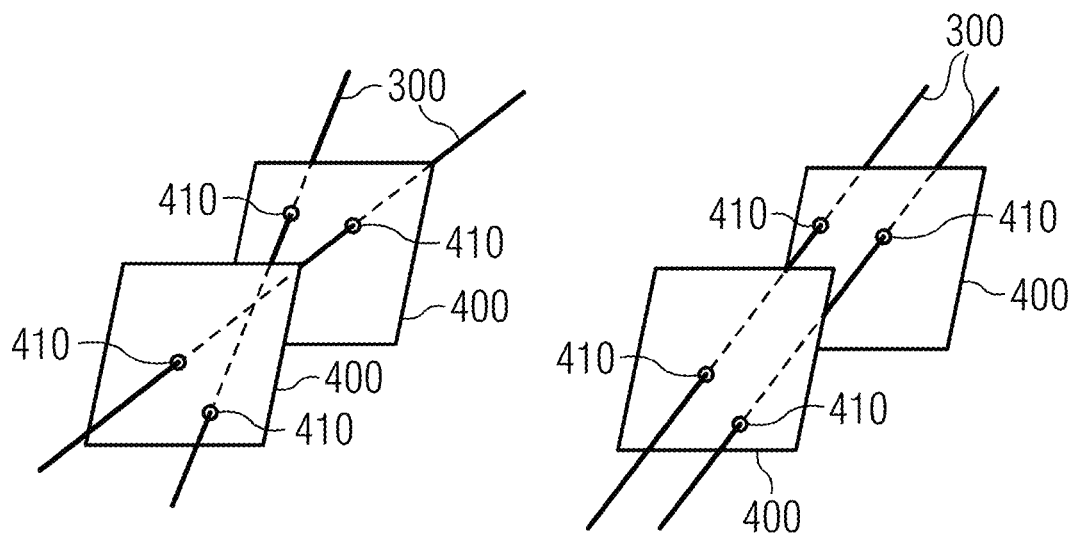
FIG. 3 illustrates circumstances of a method according to prior art involving N=2 elongate guide members and N=2 first spatial imaging planes.

FIG. 3 illustrates circumstances of a known imaging method according to prior art involving N=2 elongate guide members 300 and N=2 first spatial imaging planes 400.

More specifically, FIG. 3 illustrates two different cases involving identical intersections 410 on two tracking slices 400, but yet, resolution of individual needles 300 is ambiguous.

For example, interpretation of the intersections 410 of the two tracking slices 400 may yield two different sets of straight lines, or needles 300, as indicated by the lines drawn through the known intersections 410 with the tracking slices 400. It is thus evident that two tracking slices 400 are not enough to unambiguously determine two individual needles 300.

Figure 4:
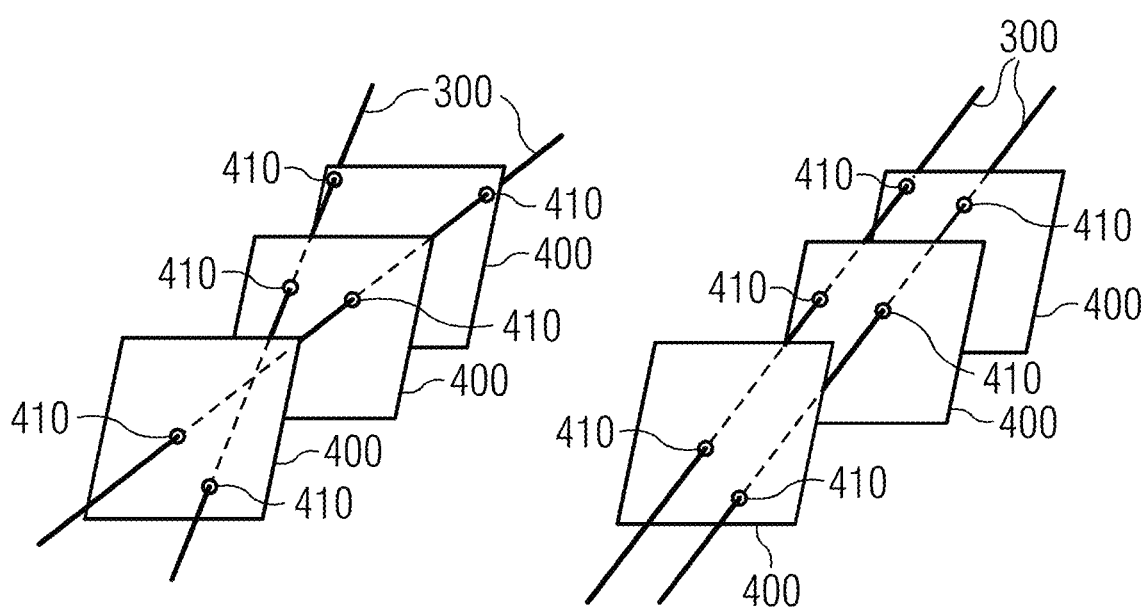
FIG. 4 illustrates circumstances of the method according to various embodiments concerning the establishing and determining acts and involving N=2 elongate guide members and N+1=3 first spatial imaging planes.

FIG. 4 illustrates circumstances of the method 100 according to various embodiments concerning the establishing 102 and determining 104 acts. The case illustrated in FIG. 4 involves N=2 elongate guide members and N+1=3 first spatial imaging planes.

Two different cases are shown involving different intersections 410 on three tracking slices 400, respectively. It is evident that the three tracking slices 400 per case unambiguously identify a spatial position/orientation of the two needles 300.

This rule may be extrapolated linearly.

For any number N of needles 300 in consideration used at the same time, N+1 tracking slices 400, each having N intersections 410, are to be created to unambiguously identify all the needles 300.

The following is undertaken in order to automatically follow a needle 300 during measurement.

According to FIG. 4, three (e.g., N+1) tracking slices 400 are established to respectively have two (e.g., N) intersections 410 with the two (e.g., N) needles 300.

The above remarks regarding parallel spatial orientations and arbitrary distance of tracking slices 400 apply analogously in the multiple needle scenario.

Those skilled in the art will appreciate that it is possible to determine a respective spatial orientation of the two (e.g., N) needles 300 using simple geometry, as indicated by the lines drawn through the respective three known intersections 410 with the tracking slices 400. The intersections 410 may be represented by three-dimensional coordinates.

For example, the intersections 410 corresponding to a same needle 300 align with one another along a spatial orientation of the respective needle 300.

As indicated by dashed lines in FIG. 1, the method 100 may further include acts 108, 110 and/or 112.

In act 108, the method 100 may further include displaying the at least one second spatial imaging plane 500 of at least one of the N elongate guide members 300.

In other words, the method 100 provisions interventionists with real-time digital images by providing the real-time digital images corresponding to systematically positioned two-dimensional planes (e.g., the at least one second spatial imaging plane, or display slice 500) in a three-dimensional image space, such as supplied by various spatial imaging techniques like computer tomography (CT) or magnetic resonance imaging (MRI). This systematic positioning of the display slices 500 is guided by the elongate guide members 300.

For example, the above-mentioned spatial imaging techniques readily provide a three-dimensional image space formed of parallel image slices from which the at least one display slice 500 may be derived. For example, a display slice 500 may be formed by using or copying the image content of the three-dimensional image space that coincides spatially with the two-dimensional plane of the at least one display slice 500 as or into the at least one display slice 500.

This enables continuous monitoring of the particular needle(s) 300 along the respective path(s) (e.g., on a respective display slice 500) and within a surrounding body portion of interest during the whole clinical intervention procedure. For example, this improves a usability of a user interface of a device that is configured to perform the method 100, as it is much easier for an interventionist to understand a digital image content of a properly positioned and oriented display slice 500 rather than a digital image content dispersed over a set of parallel image slices that respectively intersect with this display slice 500.

In addition, the method 100 enables simultaneous and continuous monitoring of two or more needles 300 along respective paths and within a surrounding body portion of interest during the whole clinical intervention procedure.

Accordingly, in both single and multiple needle scenarios, continuous monitoring is achieved through automatic re-alignment of a spatial position/orientation of the respective display slice 500 during the intervention procedure in order to keep all the needles 300 involved visible on a respective display slice 500 all the time. The continuous needle visibility is of crucial importance during clinical use cases like tissue removal, etc.

In addition, this reduces a time necessary for insertion of needles 300, as these remain visible all the time and do not require frequent manual re-adjustment, which conventionally may have required re-adjustment of corresponding tracking slices 400.

Since needles 300 may be moved constantly during a clinical intervention, it is possible that some intersections 410 between the respective needle 300 and the tracking slices 400 disappear from the respective tracking slice 400.

Thus, in act 110, the method 100 may further include, in response to a trigger event, d) detecting if each of the first spatial imaging planes 400 still has an intersection 410 with each of the N elongate guide members 300.

Those skilled in the art will appreciate that for performing d), a same or similar known method may be used as for performing a), and that the detecting 110 may be based on the tracking slices 400 having known spatial positions/orientations.

For example, the trigger event may include a lapse of a timer and/or an indication that at least one of the intersections 410 has moved within a corresponding tracking slice 400 in excess of a given threshold.

Those skilled in the art will appreciate that the detecting 110 under timer control will provide a simple but close monitoring of needle's movement, whereas the demand-driven detecting 110 in response to an indication of movement may reduce a workload of an underlying processing device 202 (see below in connection with FIG. 7) arranged to perform the detecting 110.

For example, an indication of movement may arise if at least one intersection 410 between a needle 300 and a tracking slice 400 has moved away within that tracking slice 400 from a last known position in excess of a given distance threshold. Alternatively or additionally, an indication of movement may arise if at least one intersection 410 may not be retrieved anymore within a given distance threshold from the last known position.

The method 100 may further include proceeding at act 0 in response to detecting 110 that each of the first spatial imaging planes 400 has an intersection 410 with each of the N elongate guide members 300.

In other words, if a complete set of N intersections 410 may be found per tracking slice 400 in the detecting 110 act, the method proceeds at act 104 to determine a spatial orientation of each of the N needles 300 based on the intersection 410 of the respective needle 300 with each of the tracking slices 400.

Figure 5:
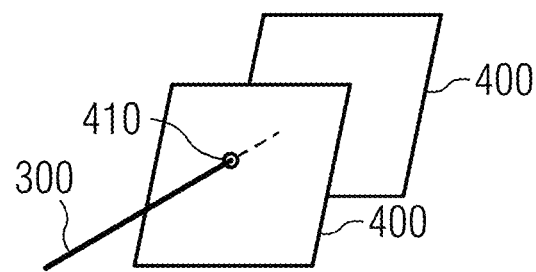
FIG. 5 illustrates circumstances of the method according to various embodiments concerning the displacing act of the method of FIG. 1.

FIG. 5 illustrates circumstances of the method 100 according to various embodiments concerning the displacing act 112.

If some of necessary intersections are missing (e.g., a particular tracking slice 400 has less then N intersections), another tracking slice 400 that captures all N intersections is to be found.

The method 100 may thus further include displacing 112, in accordance with at least one of the determined spatial orientations, the at least one of the first spatial imaging planes 400 not having an intersection 410 with each of the N elongate guide members 300 to be located closer to one of the first spatial imaging planes 400 having an intersection 410 with each of the N elongate guide members 300, and proceeding at act 0. This may be performed in response to detecting 110 that at least one of the first spatial imaging planes 400 does not have an intersection 410 with each of the N elongate guide members 300.

As used herein, "displacing" may relate to moving out of position (e.g., by translation).

This enables automatic retrieval of needles 300 once the needles 30 are "lost" (e.g., partially or entirely disappear from tracking slices 400).

After displacement of the at least one of the tracking slices 400, the method proceeds at act d) for detecting 110 if each of the tracking slices 400 (e.g., including the displaced tracking slice(s) 400) has an intersection 410 with each of the N needles 300.

For example, the displacing 112 of a tracking slice 400 may be carried out repeatedly to provide that the displaced tracking slice 400 captures all N intersections 410.

For example, the one of the first spatial imaging planes 400 having an intersection 410 with each of the N elongate guide members 300 may have a largest spacing, in accordance with the at least one of the determined spatial orientations, relative to the at least one of the first spatial imaging planes 400 not having an intersection 410 with each of the N elongate guide members 300.

In other words, the tracking slice 400 to be displaced would automatically be displaced towards the tracking slice 400 that is closest to the entry point(s) of the needle(s) 300 in the skin surface of the patient who undergoes the intervention procedure.

Figure 6:
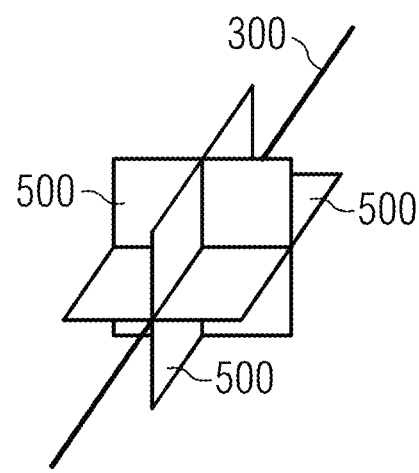
FIG. 6 illustrates circumstances of the method according to various embodiments concerning the identifying act of the method of FIG. 1.

FIG. 6 illustrates circumstances of the method 100 according to various embodiments concerning the identifying act 106.

The identifying 106 at least one second spatial imaging plane 500 may include identifying 1062 three mutually orthogonal second spatial imaging planes 500 along or perpendicular to the respective determined spatial orientation of each of the N elongate guide members 300.

Those skilled in the art will appreciate that it is possible to determine a spatial orientation of each of the N elongate guide members 300 (e.g., needles) using simple geometry, as indicated in FIG. 2 by the line drawn through the two known intersections 410 with the tracking slices 400. The intersections 410 may be represented by three-dimensional coordinates.

More specifically, in a three-dimensional Cartesian space, a linear function or line (x, y, z) passing through points ($x_0$, $y_0$, $z_0$) and ($x_1$, $y_1$, $z_1$)$_{may}$ be defined as follows:

$$x = x_0 + (x_1 - x_0)t$$

$$y = y_0 + (y_1 - y_0)t$$

$$z = z_0 + (z_1 - z_0)t$$

$$\forall -\infty < t < +\infty$$

A spatial orientation of the line is thus given by the vector:

$$(x_1 - x_0, y_1 + y_0, z_1 - z_0)$$

A display slice 500 including the given line may be determined for any chosen point ($x_0$, $y_0$, $z_0$) on the line and any arbitrary vector (a, b, c) as follows (e.g., point direction form):

$$a(x - x_0) + b(y - y_0) + c(z - z_0) = 0$$

A display slice 500 perpendicular to the given line may be determined for two arbitrary points ($x_0$, $y_0$, $z_0$) and ($x_1$, $y_1$, $z_1$) on the given line, and a third arbitrary point ($x_2$, $y_2$, $z_2$) on the plane including the line as follows (e.g., three point form):

$$\begin{vmatrix} x - x_0 & y - y_0 & z - z_0 \\ x_1 - x_0 & y_1 - y_0 & z_1 - z_0 \\ x_2 - x_0 & y_2 - y_0 & z_2 - z_0 \end{vmatrix} = 0$$

A display slice 500 perpendicular to the two given, mutually perpendicular planes may be determined based on an arbitrary point ($x_0$, $y_0$, $z_0$) on the given line and a vector (a, b, c) that lies on the line. In this case, the plane will be perpendicular to vector (a, b, c), includes the given point ($x_0$, $y_0$, $z_0$), and will be perpendicular to the given perpendicular planes:

$$a(x-x_0)+b(y-y_0)+c(z-z_0)=0$$

Accordingly, up to three display slices 500 may be displayed to the user per needle 300 with the entire needle 300 shown on two of these display slices 500 that are not orthogonal to the respective needle 300, while a third display slice 500 merely shows an intersection with the needle 300.

Figure 7:
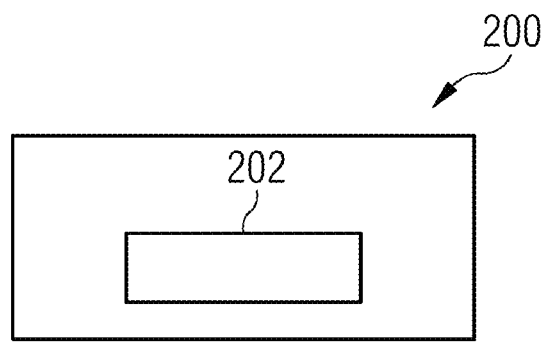
FIG. 7 illustrates an imaging device according to various embodiments.

FIG. 7 illustrates an imaging device 200 according to various embodiments.

The imaging device 200 is for performing a method 100 that is guidable by N elongate guide members 300 and seeks to provide meaningful real-time visualization of the elongate guide members 300 within a surrounding body portion of interest during a clinical intervention.

A most general embodiment of the imaging device 200 includes at least one processing device 202 being arranged for performing the method acts 102, 104, and 106.

Act 102 involves a) establishing N+1 first spatial imaging planes 400 each having an intersection 410 with each of the N elongate guide members 300.

For example, the first spatial imaging planes 400 may be arranged parallel to one another.

Act 104 involves b) determining a spatial orientation of each of the N elongate guide members 300 based on the intersection 410 of the respective guide member with each of the first spatial imaging planes 400.

Act 106 involves c) identifying at least one second spatial imaging plane 500 along or perpendicular to the respective determined spatial orientation of each of the N elongate guide members 300.

Additionally, the at least one processing device 202 may further be arranged for performing the method 100 according to various embodiments.

In other words, those skilled in the art will appreciate that the imaging device 200 and the above-defined method 100 have corresponding features.

This confers to the imaging device 200 the same technical effects and advantages described above in relation with the method 100.

While exemplary embodiments incorporating the principles of the present disclosure have been disclosed hereinabove, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this disclosure pertains and that fall within the limits of the appended claims.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of operating an imaging device, the method being guidable by N elongate guide members, the N elongate guide members being physical elongate guide members, the method comprising:
   establishing N+1 first spatial imaging planes each having an intersection with each of the N elongate guide members;
   determining a spatial orientation of each of the N elongate guide members based on the intersection of the respective guide member with each of the first spatial imaging planes;
   identifying at least one second spatial imaging plane along the respective determined spatial orientation of each of the N elongate guide members;
   acquiring an image along a second spatial imaging plane of the at least one second spatial imaging plane; and
   displaying the image,
   wherein the number N of elongate guide members is a positive integer.

2. The method of claim 1, further comprising detecting, in response to a trigger event, if each of the first spatial imaging planes still has an intersection with each of the N elongate guide members.

3. The method of claim 2, wherein the trigger event comprises a lapse of a timer, an indication that at least one of the intersections has moved within the corresponding first spatial imaging plane in excess of a given threshold, or the lapse of the timer and the indication that at least one of the intersections has moved within the corresponding first spatial imaging plane in excess of the given threshold.

4. The method of claim 2, further comprising proceeding to the determining of the spatial orientation of each of the N elongate guide members in response to detecting that each of the first spatial imaging planes has an intersection with each of the N elongate guide members.

5. The method of claim 2, further comprising:
   in response to detecting that at least one of the first spatial imaging planes does not have an intersection with each of the N elongate guide members:
      displacing the at least one of the first spatial imaging planes not having an intersection with each of the N elongate guide members to be located closer to, in accordance with at least one of the determined spatial orientations, one of the first spatial imaging planes having an intersection with each of the N elongate guide members; and
      proceeding to the detecting if each of the first spatial imaging planes still has an intersection with each of the N elongate guide members.

6. The method of claim 5, wherein the one of the first spatial imaging planes having an intersection with each of the N elongate guide members has a largest spacing, in accordance with the at least one of the determined spatial orientations, relative to the at least one of the first spatial imaging planes not having an intersection with each of the N elongate guide members.

7. The method of claim 1, further comprising displaying the at least one second spatial imaging plane of at least one of the N elongate guide members.

8. The method of claim 1, wherein identifying at least one second spatial imaging plane comprises identifying three mutually orthogonal second spatial imaging planes along or perpendicular to the respective determined spatial orientation of each of the N elongate guide members.

9. The method of claim 1, wherein the number N of elongate guide members equals 1.

10. The method of claim 1, wherein the elongate guide members comprise a surgical needle.

11. The method of claim 1, wherein the first spatial imaging planes are arranged parallel to one another.

12. An imaging device that is guidable by N elongate guide members, the N elongate guide members being physical elongate guide members, the imaging device comprising:
at least one processor configured to:
establish N+1 first spatial imaging planes each having an intersection with each of the N elongate guide members;
determine a spatial orientation of each of the N elongate guide members based on the intersection of the respective guide member with each of the first spatial imaging planes;
identify at least one second spatial imaging plane along the respective determined spatial orientation of each of the N elongate guide members;
acquire an image along a second spatial imaging plane of the at least one second spatial imaging plane; and
display the image,
wherein the number N of elongate guide members is a positive integer.

13. The imaging device of claim 12, wherein the at least one processor is further configured to detect, in response to a trigger event, if each of the first spatial imaging planes still has an intersection with each of the N elongate guide members.

14. The imaging device of claim 13, wherein the trigger event comprises a lapse of a timer, an indication that at least one of the intersections has moved within the corresponding first spatial imaging plane in excess of a given threshold, or the lapse of the timer and the indication that at least one of the intersections has moved within the corresponding first spatial imaging plane in excess of the given threshold.

15. The imaging device of claim 13, wherein the at least one processor is further configured to proceed to the determination of the spatial orientation of each of the N elongate guide members in response to detection that each of the first spatial imaging planes has an intersection with each of the N elongate guide members.

16. The imaging device of claim 13, wherein the at least one processor is further configured to:
in response to detection that at least one of the first spatial imaging planes does not have an intersection with each of the N elongate guide members:
displace the at least one of the first spatial imaging planes not having an intersection with each of the N elongate guide members to be located closer to, in accordance with at least one of the determined spatial orientations, one of the first spatial imaging planes having an intersection with each of the N elongate guide members; and
proceed to the detection if each of the first spatial imaging planes still has an intersection with each of the N elongate guide members.

17. The imaging device of claim 16, wherein the one of the first spatial imaging planes having an intersection with each of the N elongate guide members has a largest spacing, in accordance with the at least one of the determined spatial orientations, relative to the at least one of the first spatial imaging planes not having an intersection with each of the N elongate guide members.

* * * * *